United States Patent [19]

Holsworth et al.

[11] Patent Number: 4,478,073
[45] Date of Patent: Oct. 23, 1984

[54] METHOD FOR DETERMINING PARTICLE SIZE AND/OR DISTRIBUTION

[75] Inventors: Richard M. Holsworth, Westlake; Theodore Provder, Olmsted Falls, both of Ohio

[73] Assignee: SCM Corporation, New York, N.Y.

[21] Appl. No.: 460,731

[22] Filed: Jan. 25, 1983

[51] Int. Cl.³ .......................................... G01N 15/04
[52] U.S. Cl. ................................. 73/61.4; 73/432 PS
[58] Field of Search .......................... 73/61.4, 432 PS; 494/10, 27

[56] References Cited

U.S. PATENT DOCUMENTS

| | | | |
|---|---|---|---|
| 2,956,434 | 10/1960 | Donoghue | 73/432 PS |
| 3,237,455 | 3/1966 | Slater | 73/432 PS |
| 3,243,106 | 3/1966 | Atherton et al. | |
| 3,475,968 | 11/1969 | Jones | 73/432 PS |
| 4,055,076 | 10/1977 | Tropea | 73/61.4 |
| 4,311,039 | 1/1982 | Koehler et al. | 73/61.4 |

OTHER PUBLICATIONS

Anal. Chim. Acta 38, (1967), pp. 143-146, Jones et al., Particle Size Analysis of Inorganic Pigments.
Proc. Soc. Analyt. Chem., Apr. 5, 1966, pp. 116-117, Jul. 1966, "The ICI-Joyce-Loebl Disc Centrifuge", Jones.
Powder Technology, 13, (1976), pp. 215-221, "Particle Size Determination of Pigments with a Disc Centrifuge", Brugger.
Pigments Handbook, III-A-d-2-ii, pp. 53-62, "Centrifugal Sedimentation", Fraser.
Powder Technology 1, (1967), pp. 103-115; "The Accuracy and Precision of the Centrifugal-Disc Photosedimentometer Method of Particle Size Analysis", Burt.
Jour. Oil & Colour Chem. Assoc., vol. 50, (1967), pp. 594-614; "Size Analysis of Organic Pigments using the ICI-Joyce-Loebl Disc Centrifuge", Beresford.
Jour. Soc. Dyers & Colourists, 80, (1964), pp. 521-526, "The Measurement of Particle Size and its Practical Significance in Vat-Dye Quality", Atherton et al.
Colloid and Polymer Sci. 257, (1979), pp. 522-532; "Sedimentation Analysis of Aqueous Polymer Dispersions with a Disc Centrifuge", Langer.
Particle Size Analysis Conference, (1966), pp. 242-257; "The Two-Layer Method of Centrifugal Particle Size Analysis", Scarlett et al.
Chemical Analysis, "Direct Characterization of Fine Particles", Kaye, vol. 61, John Wiley & Son (1981), pp. 189-226.
Colloid & Polymer Science, 258, pp. 1077-1985 (1980), CODEN CPMSS, "Schnelle Dichtegradienten-Zentrifugation Dispergierter Teilchen, Lange.
Alex. Dissertation for PhD in Engineering, Jul. 15, 1972, Univ. of Karbruhe, "Zur Genaulgkeit der Teilchengrossenanalyse durch Sedimentation im Zentrifugalfeld".

*Primary Examiner*—Gerald Goldberg
*Assistant Examiner*—Joseph W. Roskos
*Attorney, Agent, or Firm*—R. A. Sturges; M. H. Douthitt

[57] ABSTRACT

There is provided a new method for analysis of the size and/or distribution of particles emanating from a mother liquid by sedimentation in a rotating disc centrifuge, particularly a photosedimentometer. The method is characterized in that the spin fluid or medium is formed externally of the disc as distinct from being formed within the disc while it is rotating. The externally prepared spin medium is formed from at least two miscible liquids of different densities for example, methanol and water, in a manner such that they are substantially incompletely mixed whereby a density gradient is established in the spin medium. Thereafter the spin medium is injected into the disc while spinning at a given speed, and later the mother liquid is injected. Results are closely comparable to the buffered line start method described in U.S. Pat. No. 3,475,968.

18 Claims, 8 Drawing Figures

(PRESENT METHOD)

METHOD FOR DETERMINING PARTICLE SIZE AND/OR DISTRIBUTION

This invention relates to a method for analyzing particle size and/or distribution especially in a liquid medium such as a latex or pigment slurry.

BACKGROUND OF THE INVENTION AND PRIOR ART

The disc centrifuge photosedimentometer has proved to be an excellent instrument for providing particle size and particle size distribution information to pigment and latex manufacturers and formulators. In use, a disc centrifuge photosedimentometer operates by forcing particles (generally of less than about $2\mu$ in size) under high centrifugal force radially outwardly through a spin fluid or medium. Here they segregate into sizes, the larger traversing the medium more quickly and the smaller taking a longer time. In general, bands of particles, of approximately the same size are created in the medium and can be measured optically with the aid of light or other suitable radiation to which the particles are opaque traversing the spin medium in an axial direction. The bands so created intercept the radiation and can be analyzed and the data obtained converted to particle size and/or distribution curves.

A particularly satisfactory method for photosedimentometric analysis is that described and claimed in U.S. Pat. No. 3,475,968 dated Nov. 4, 1969. U.S. Pat. No. 4,311,039 dated Jan. 19, 1982 describes and claims an apparatus which is especially effective in practicing the method of the aforesaid U.S. Pat. No. 3,475,968. The apparatus of the aforesaid U.S. Pat. No. 4,311,039, with or without modification, can be used most satisfactorily in practicing the present method. Thus, the disclosure of U.S. Pat. No. 4,311,039 is incorporated herein by reference.

The homogeneous, the line start and the buffered line start methods are well known. The latter two systems involve preparation of spin fluids or spin media in situ, i.e., during high speed rotation. Reference may be had to Chemical Analysis, "Direct Characterization of Fine Particles" by B. H. Kaye, Volume 61, John Wiley & Sons, 1981, pages 189–226; Schnelle Dichtegradienten - Zentrifugation dispergierter Teilchen, Lange, Colloid & Polymer Sci., 258, p. 1077–1085 (1980) CODEN CPMSS); "Zur Sedimentationsanalyse wassriger Kunststoffdispersionen mit der Scheibenzentrifuge" Langer, Colloid and Polymer Sci., 257, p. 522–532 (1979) CODEN CPMSE; Zur Genauigkeit der Teilchengrossenanalyse durch Sedimentation im Zentrifugalfeld" Alex, Dissertation for PhD in Engineering 15 Jul 1972 Universitat Kalsruhe. Reference may also be had to the following U.S. Pat. Nos. 2,956,434 Donoghue; 3,237,455 Slater; 3,243,106 Atherton, and the following articles; Jones et al "Particle Size Analysis of Inorganic Pigments" Anal. Chim Acta 38, (1967) 143–146; Proc. Soc. Anal. Chem., Particle Size Analysis Group, July 1966 "The ICI—Joyce Loebl Disc Centrifuge", Jones; Powder Technology, 13 (1976), 215–221 "Particle Size Determination of Pigments with a Disc Centrifuge, " Brugger; "Centrifugal Sedimentation, Fraser, Pigments Handbook III-A-d-2-ii, pp. 53–62; "The Accuracy and Precision of the Centrifugal Disc Photosedimentometer Method of Particle Size Analysis", Burt, Powder Technology, 1, (1967) 103–115; "Size Analysis of Organic Pigments using the ICI—Joyce-Loebl Disc Centrifuge", Beresford, Jour. Oil & Color Chem. Assoc. Vol. 50, (1967) 594–614; "The Measurement of Particle Size and its Practical Significance in Vat Dye Quality", Atherton et al, J. Soc. Dyers Colourists 80, p. 521–526 (1964); G. P. Langer, "Sedimentation Analysis of Aqueous Polymer Dispersions with a Disc Centrifuge; " Colloid and Polymer Sci., 257, 522–532 (1979); and Scarlett et al, "The Two Layer Method of Particle Size Analysis", Particle Size Analysis Conference, 1966 pages 242–267.

From the foregoing patents and literature, it will be seen that the industry method of choice is the Joyce-Loebl buffered line start method for particle size determination. Because of its improved structure and control means the apparatus described and claimed in U.S. Pat. No. 4,311,039 is especially useful in carrying out the buffered line start method.

We have found a new and alternative method for making centrifugal disc photosedimentometric analyses which also allows simplification in the aforesaid improved apparatus as well as the apparatus of U.S. Pat. No. 3,475,968. Power interrupting means utilized in both devices can, if desired, be eliminated. In any event, such power interrupting means are not used in practicing this invention. Moreover, the results obtained according to the new method as will be shown herein, are virtually identical with the results obtained with the apparatus of U.S. Pat. No. 4,311,039 using the buffered line start method described in U.S. Pat. No. 3,475,968 and in much of the prior art mentioned above. Basically, the new method contemplates formation of the spin fluid including a density gradient, externally of the disc and injecting such externally formed spin fluid into the open center of the disc while it is spinning at a predetermined speed.

BRIEF STATEMENT OF THE INVENTION

Briefly stated, therefore, the present invention is in a method for the analysis of the size and/or distribution of particles emanating from a mother liquid, or sample, by sedimentation in a rotating disc centrifuge. The method comprises the steps of forming externally of said disc a liquid spin medium containing at least two miscible liquids of different densities in substantially incompletely mixed condition whereby a density gradient is established within said spin medium, thereafter injecting said externally formed spin medium into said centrifuge disc while rotating said disc about its axis (either horizontally or vertically disposed) at a predetermined speed, and subsequently injecting into said disc centrifuge while spinning at said predetermined speed, a mother liquid, or sample, containing particles the size and/or distribution of which are to be determined. A particularly satisfactory spin medium is formed from incompletely mixed water and methanol.

BRIEF DESCRIPTION OF THE DRAWINGS

The invention may be better understood by having reference to the annexed drawings wherein.

DETAILED DESCRIPTION OF THE INVENTION AND SPECIFIC EXAMPLES

Much of the literature, and particularly that authored by M. H. Jones and in his U.S. Pat. No. 3,475,968, has addressed the problem of "streaming". In "streaming" particles from a mother liquid or sample encounter an interface with the spin fluid under high centrifugal force. The spin fluid, having a different density from the mother liquid or sample, the concentration of the particles and the nature of the contact between the sample and the spin fluid in the spinning disc presents an unstable environment for particle movement and the particles tend suddenly to break through this interface and "stream" toward the outer periphery of the disc. Once this phenomenon occurs, it is not possible to obtain accurate results. Hence, it was determined that to avoid "streaming" a density transition zone or density gradient into the higher density fluid needed to be provided to obviate the problem of streaming. This worked well and prevented "streaming". Jones in U.S. Pat. No. 3,475,968 developed his density gradient in situ within the spinning disc by separately injecting (by syringe) first and second liquids which formed distinct layers. Then he momentarily interrupted the power supply to the motor driving the centrifugal disc thereby causing the second or lighter density liquid to begin to blend with the first. When the sample containing the particles was later injected and positioned on top of the spin fluid the particles moved from the mother liquid into a spin medium of gradually changing density. This avoided streaming.

We have discovered an alternative method of providing a spin medium having the necessary density gradient to prevent streaming. Instead of preparing the density gradient in situ in the centrifugal disc, we prepare a spin medium having a density gradient ex situ. This is accomplished most conveniently by sequentially inspiring the gradient forming liquids into a common hypodermic syringe, for example a standard 5, 10, 20 or 30 ml syringe.

It has been found that for best results, the size of the syringe used should approximate the volume of the ex situ formed spin medium to be injected. The reason for this is that if the barrel has too large a diameter or is axially too long relative to the volume of spin medium being injected, the quality of the density gradient is adversely affected, i.e., too much mixing of the liquids may occur on inspiration of the spin medium ingredients as well as on expiration thereof from the syringe.

Figure 7:
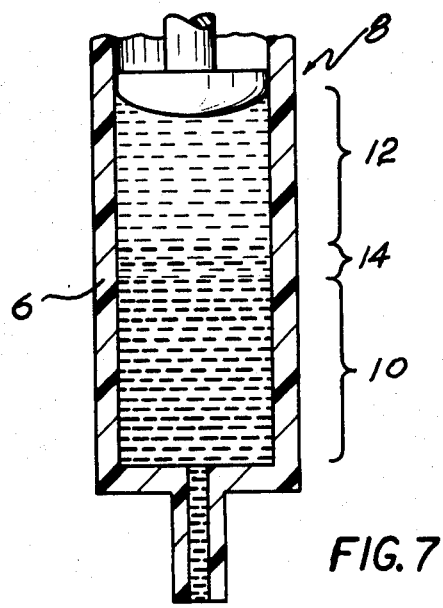
FIG. 7 is a digrammatic representation of a syringe showing a spin fluid of two different liquids, e.g., methanol and water, with a density gradient between where the liquids are partially mixed.
Figure 8:
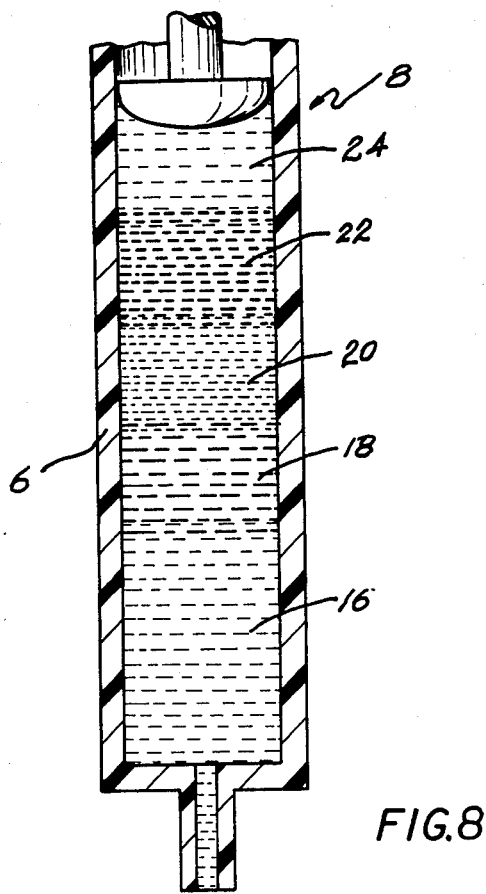
FIG. 8 is a diagrammatic representation of a syringe showing a spin fluid formed of 5 different liquids arranged vertically with the most dense liquid on the bottom and the progressively less dense liquids disposed in order of decreasing density above.

In FIGS. 7 and 8 we have shown in diagrammatic form the formation of a density gradient within the barrel 6 of a syringe 8. Any two or more liquids of different density 10 and 12 may be used providing the liquids are mutually soluble or become so. The less dense liquid 12 is preferably, although not essentially, inspired up through the denser liquid 10. A given liquid of the liquid pair may comprise two components, e.g., an aqueous solution of an alcohol in water, e.g., 50% methanol/water, or mineral acid/water, or sugar/water solution with alcohol. For most purposes, two miscible liquid compounds of different density are used, although a spin medium may be made of three or more different liquid compounds, e.g., methanol (MeOH), methyl ethyl ketone and water. Solutions of a normally solid material as a solute in a solvent, e.g., sugar in water, may be used as one of the liquids. The existence of a density gradient in the syringe is easily verified by dyeing one of the liquid components and drawing the spin medium ingredients sequentially into the syringe, the denser 10, preferably being inspired first. In the central or interfacial portion 14 of the body of fluid, the color intensity will change from the intense color of the dyed liquid through a gradation of color indicated in FIG. 7 by the blending of the respective lighter and heavier dotted lines in the central portion 14 of the barrel to the colorless portion indicative of the incomplete mixing and the presence of a density gradient. The prior art listed above discloses numerous examples of solutions or liquids which may be used in accordance with this invention to form a density gradient ex situ.

The method of the present invention is applicable to multiple layers of miscible fluids of differing densities. FIG. 8 shows in diagrammatic form a spin fluid composition in the barrel 6 of a syringe 8 composed of 5 layers of liquids of different density proceeding upwardly in the order of decreasing density. The lowest layer 16 may be ethylene glycol. The next layer 18 may be water, the next 20, 50:50 isopropanol/water, the next 22, ethanol and the top layer 24 methanol. The method of this invention may also be practiced in using a first injection into the disc of a homogeneous liquid, e.g., water or water/sugar, followed by injection thereover of an ex situ prepared spin fluid. In this event, the homogeneous liquid desirably has a higher density than the subsequently injected ex situ prepared spin fluid. It is further a part of this invention that a plurality of ex situ prepared spin fluids each possessing its density gradient may be sequentially injected at the same constant speed of disc rotation and used herein. The denser spin fluid in this case is injected first.

There are several advantages to multiple layer spin fluids. This extends the dynamic range of particle size accessible to analysis in a single run. This modification of the present invention segregates heterogeneous particles of varying sizes and having different densities. By using the modified method with multiple layers where the density of the spin fluid varies along a gradient, each particle will have not only a unique size and density, but also a unique appearance time at the detector.

Referring now to FIGS. 1, 2, 3 and 4, 5 and 6, there are here shown graphs of detector response versus time.

Figure 1:
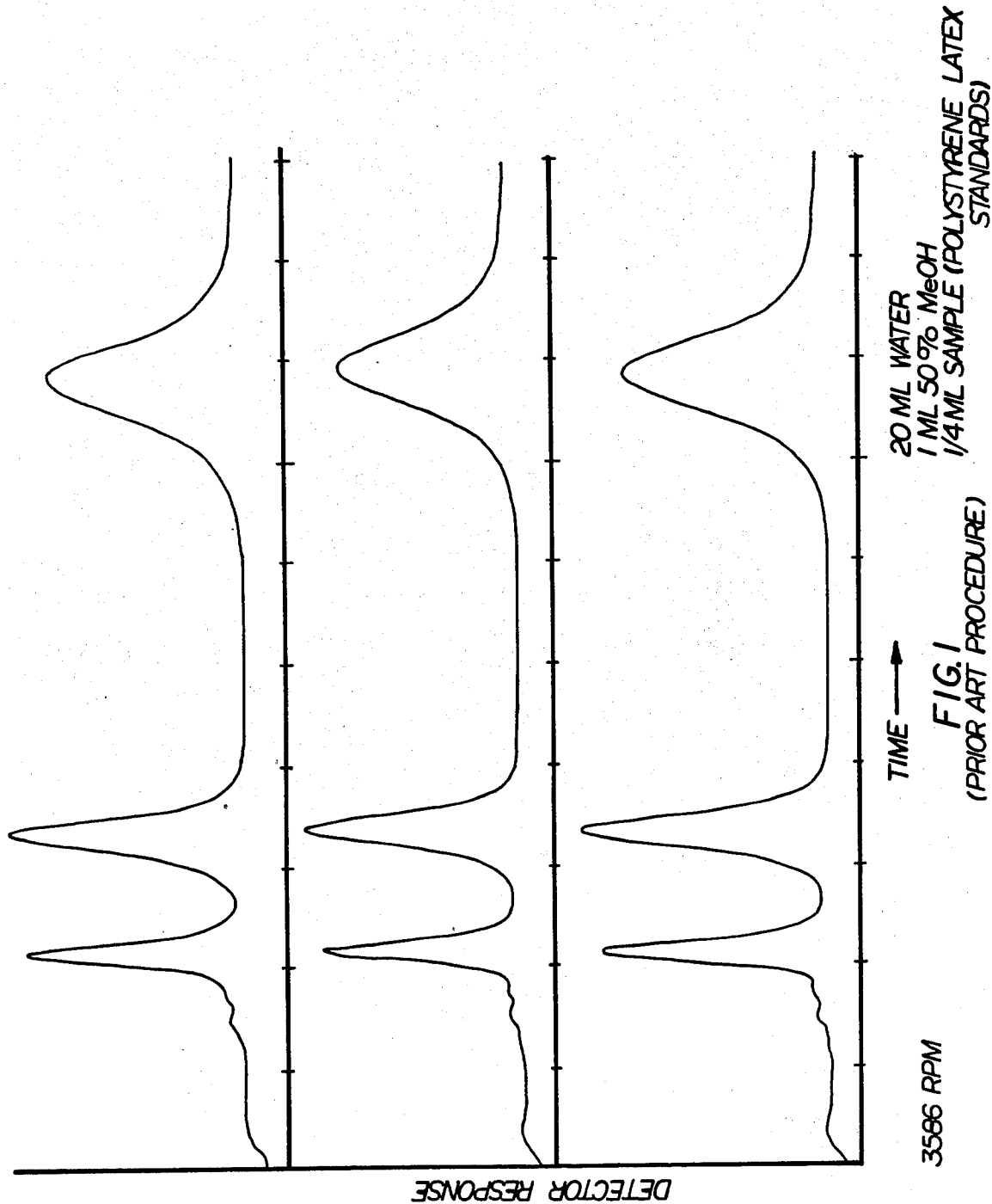
FIG. 1 is a chart representing the particle size and distribution of a mixture of particles of polystyrene of standard sizes as a latex as determined by the buffered line start method in the apparatus shown and described in U.S. Pat. No. 4,311,039. Three runs are illustrated.
Figure 2:
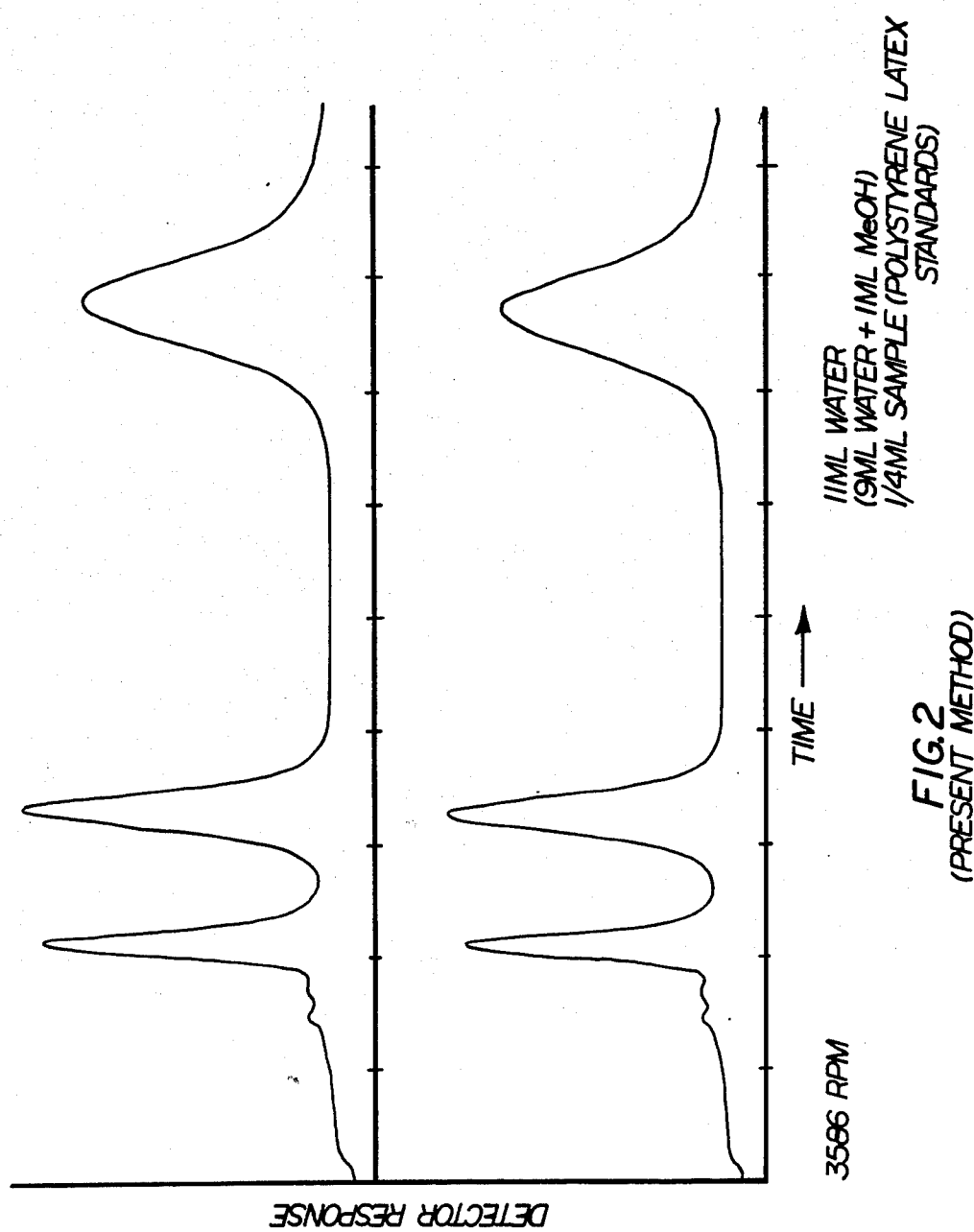
FIG. 2 is a chart representing the particle size and distribution of a mixture of particles of polystyrene of standard sizes as a latex as determined by the external density gradient method of the present invention in the apparatus shown and described in U.S. Pat. No. 4,311,039 omitting the interruption of the driving force with the programmable timer 48 (FIG. 1 of the patent). Two runs are shown.
Figure 3:
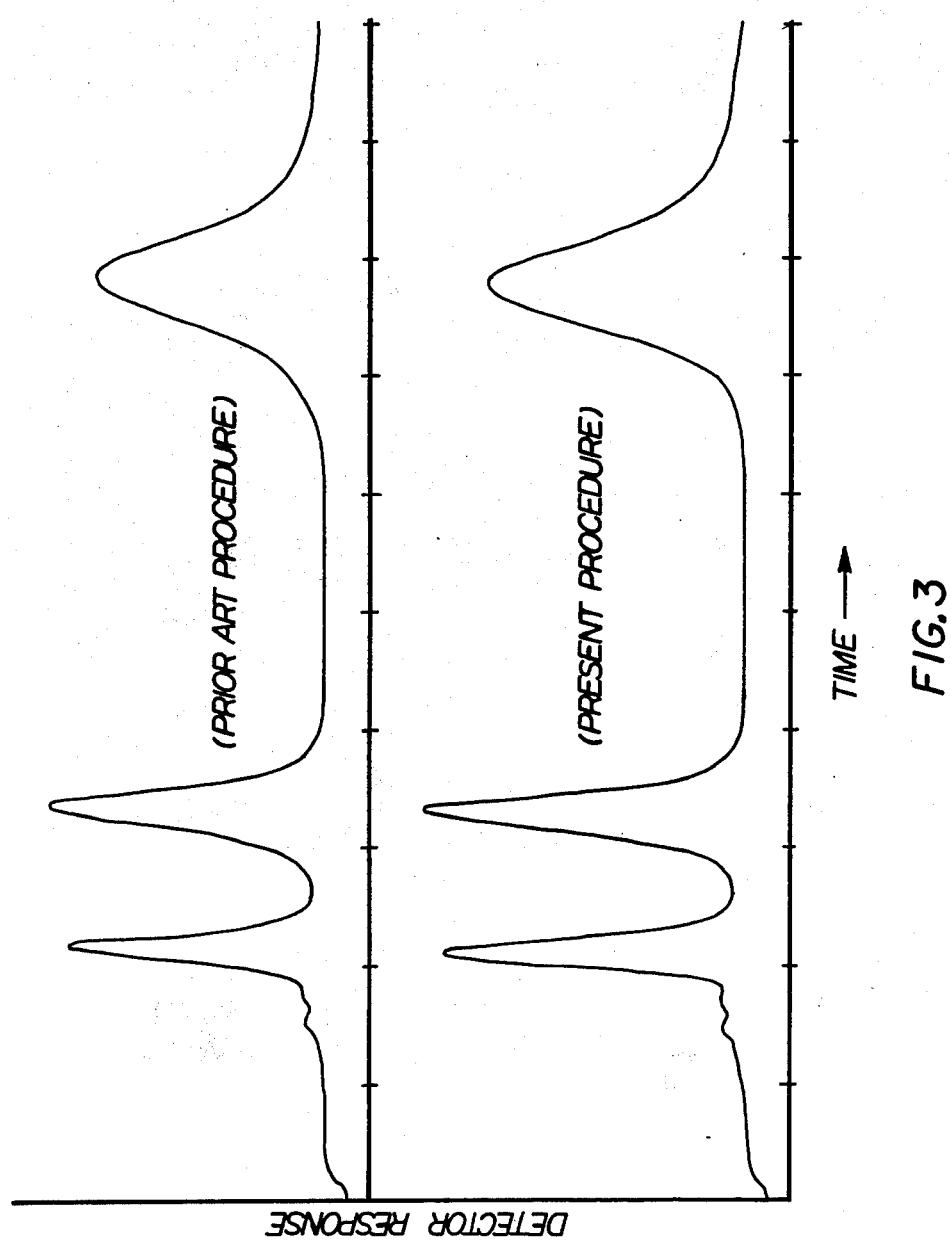
FIG. 3 is a chart comparing the respective results of FIGS. 1 and 2 on the same sheet.

In FIGS. 1-4 the speed of the disc was fixed at 3,586 rpm. In FIG. 5, it was preset at 10,450 rpm. Precise speed control is easily achieved with the apparatus shown in U.S. Pat. No. 4,311,039. The spin fluid volume in each of FIGS. 1-4 was 20 milliliters and the sample volume was 0.25 milliliter. In FIG. 5, the spin fluid volume was 15 milliliters. The profiles shown in FIG. 1 were three replicates using the buffered line start method described in U.S. Pat. No. 3,475,968. FIG. 2 shows two replicates using the ex situ method hereof. The test sample used in FIGS. 1, 2 and 3 was formed of 3 polystyrene standards having known particle sizes of $1.091\mu$, $0.822\mu$ and $0.497\mu$ respectively. The peaks received in FIGS. 1, 2 and 3 correspond to particle sizes of $1.011\mu$, $0.79\mu$ and $0.50\mu$, respectively. As can be seen, particularly in FIG. 3 where the respective methods of analysis are directly compared under like conditions, the results obtained by the ex situ method of the present invention are virtually identical with the results obtained by the prior art in situ method of forming the density gradient. The variations from the standards (the particle sizes therein having been determined by microscopy) are within tolerable limits. The test samples in FIGS. 1, 2 and 3 were from the same batch.

Figure 4:
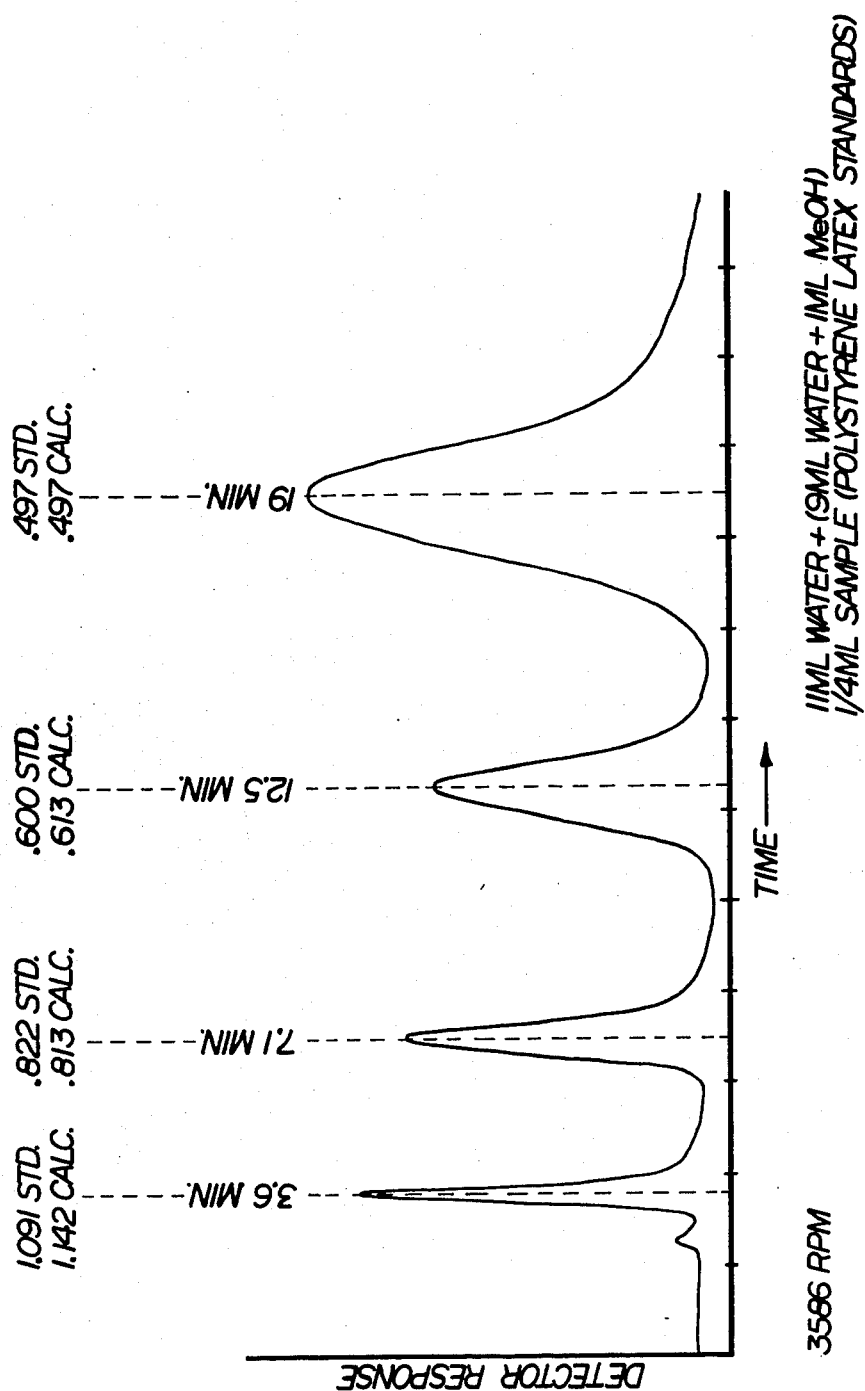
FIG. 4 is a chart representing a quantitative analysis of peak diameters for a mixture of polystyrene latex standards using the method of the present invention.
Figure 5:
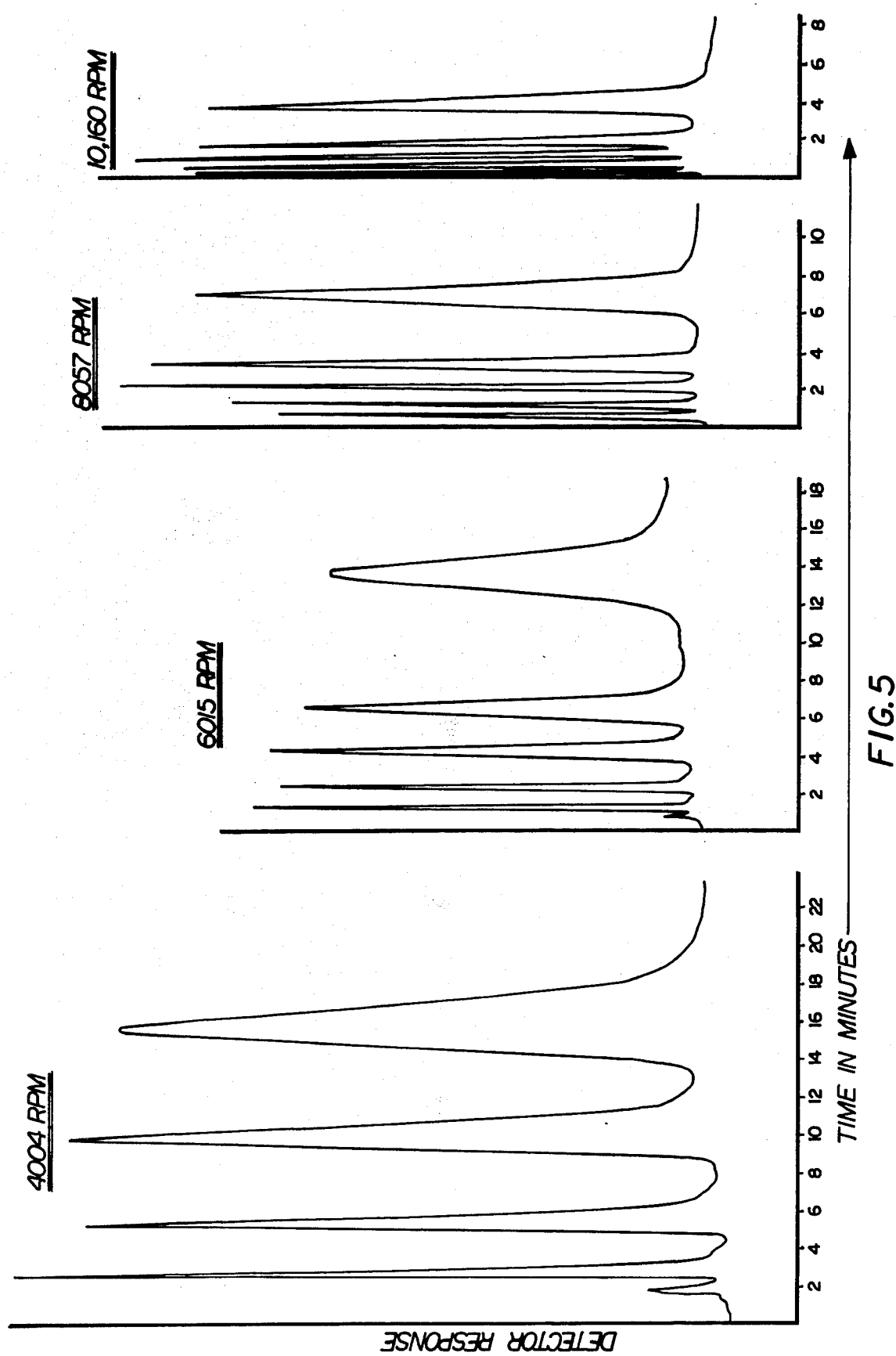
FIG. 5 shows the effect of disc speed on the time for detection of a peak representing a given particle size.

FIG. 4 shows the results obtained on another sample using a spin fluid having the volumetric composition of Example VI below and standard particle sizes of polystyrene dispersed in 50% MeOH in $H_2O$. The sample fluids in all cases were made from polystyrene dispersions in water of a predetermined particle size to about 10% solids, a drop or two from each dispersion is mixed into a 50:50 MeOH/$H_2O$ solution, about 25 ml in volume, to form the test sample. In FIG. 4, four such standards were mixed and show peaks at 3.6 minutes, 7.1 minutes, 12.5 minutes and 19 minutes in an apparatus as shown in U.S. Pat. No. 4,311,039 operated at 3,586 rpm. These peaks were calculated to be $1.142\mu$, $0.813\mu$, $0.613\mu$ and $0.497\mu$, respectively. These calculated particle sizes corresponded to microscopically determined particle sizes of $1.091\mu$, $0.822\mu$, $0.600\mu$ and $0.497\mu$, respectively. The test samples for FIGS. 1, 2 and 3 were prepared in a similar manner using the first, second and fourth standards only.

Figure 6:
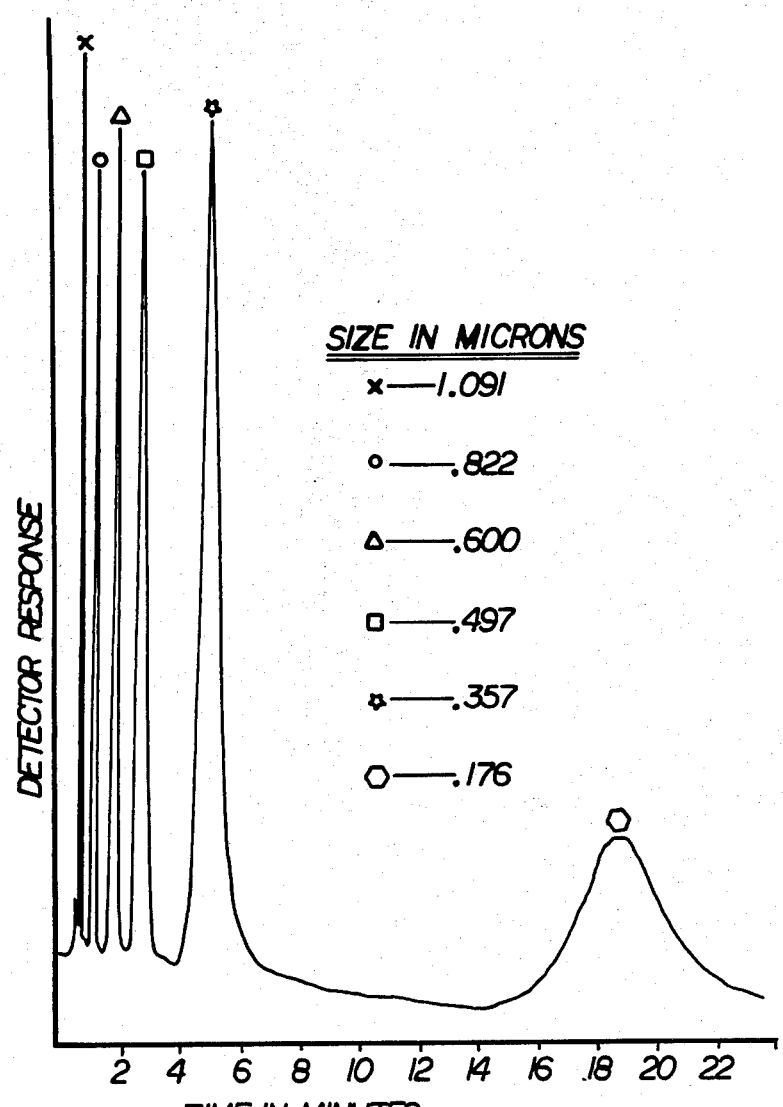
FIG. 6 is a chart representing the detector response of a sample run at 10,450 rpm containing 6 different particle sizes as determined using the method of the present invention.

In FIG. 5, following the same procedure 6 standard polystyrene particle sizes were used; namely, $1.091\mu$, $0.822\mu$, $0.600\mu$, $0.497\mu$, $0.357\mu$, and $0.176\mu$. The time in minutes for detector response at 10,450 rpm is shown in FIG. 5. FIG. 6 uses a sample containing the first 5 standards used in developing FIG. 5 and illustrates the effect of disc speed on the time required for a given particle size to show a detector response peak. The method used in FIGS. 5 and 6 is the ex situ method of the present invention.

We have found that the ex situ method hereof can be carried out over a wide range of centrifuge speeds ranging across the limits of the variable speed transmission, i.e., from about 1,500 to 11,000 rpm. At the higher rpms, e.g., 8,000 to 10,000 rpm., the ex situ method hereof appears to yield more stable particle size separations than the buffered line start method. Moreover, it is possible with the ex situ method hereof to inject successive samples into the disc cavity using the same spin fluid used for the first injected sample and still obtain stable particle size separations for samples successively injected. Minor corrections for total spin fluid volume to account for additionally injected sample volumes are required to maintain quantitative accuracy. This variation of the basic ex situ method works because of the inherent stability of the gradient produced by the ex situ method hereof. The stability obtained is due to the constancy of speed provided by the traction drive and the temperature stability produced by the Vortec cooler as described in U.S. Pat. No. 4,311,039.

It has also been found that the speed of the preferred apparatus (4,311,039) can be varied slowly, manually, to go from one rpm level to another level, e.g., 3,000 to 5,000 rpm, 5,000 to 8,000 rpm, and 8,000 to 10,000 rpm. After a sample has been run it is possible to successfully run another sample at the new rpm using the same initial spin fluid formed ex situ. This has been done at the four rpm levels exemplified above with four samples, all using the same ex situ formed spin fluid.

The following are specific examples of spin fluids which may be formed ex situ with the aid of an ordinary hypodermic syringe by carefully drawing into the barrel preferably the most dense liquid first, followed in order by the liquid or liquids in the order of decreasing density. In the preparation of the spin fluids hereof, it is desirable that the viscosities ($\eta$) of the respective liquids be relatively close, i.e., differing from each other by less than 1 poise at 20° C. Thus, pure glycerine with a viscosity at 20° C. of about 8.5 poise and water with a viscosity of about 0.01 poise do not of themselves form a satisfactory spin fluid. The difference in viscosity is too great. However, a glycerine/water solution can be used with another glycerol/water solution containing a different concentration of glycerol, or with water or an alcohol or a glycol, for example, so long as the viscosities of the liquids differ by less than 1 poise. In the preparation of the ex situ spin fluids hereof, the liquid of lower density is preferably drawn into the syringe after the liquid of higher density. In the following examples, the liquids are inspired into the syringe in the order named, the lower density liquid being drawn through the body of the higher density liquid.

EXAMPLE I

| | |
|---|---|
| Water | 11 ml |
| Water 9 ml + MeOH 1 ml (100%) | 10 ml |

EXAMPLE II

| | |
|---|---|
| Water | 20 ml |
| MeOH (100%) | 1 ml |

EXAMPLE III

| | |
|---|---|
| Water | 5 ml |
| MeOH (100%) | 1 ml |

EXAMPLE IV

| | |
|---|---|
| Ethylene glycol | 5 ml |
| Water | 1 ml |

EXAMPLE V

| | |
|---|---|
| Ethylene glycol | 5 ml |
| Water | 5 ml |

-continued

| MeOH (100%) | 1 ml |

EXAMPLE VI

| Water | 9 ml |
| MeOH (100%) | 1 ml |

The liquid compositions given above are preferred spin fluids. As indicated many other liquid compositions may be used in forming the spin fluids having an ex situ formed density gradient. Examples of these, many of which are in the prior art in connection with in situ formed density gradients, include:
Glycerol/Water - Water (varied ratios 1:20 to 20:1)
Water - Methanol/water (varied ratios 1:20 to 20:1)
Sucrose/Water - Water (varied ratios 1:20 to 20:1)
Water/Thickener (such as Cellosize) - Ammonium Polymetharcrylate (varied ratios 1:20 to 20:1)
Mineral Oil/Solvent - Solvent (varied ratios 1:20 to 20:1)
$CCl_4$/Mineral Spirits - $CCl_4$ (varied ratios 1:20 to 20:1)
Isopropanol/$CCl_4$ - Isopropanol (varied ratios 1:20 to 20:1)
Isopropanol/Hexane - Hexane (varied ratios 1:20 to 20:1)
Soluble Resin/Solvent - Solvent (varied ratios 1:20 to 20:1)

Examples from H. Lange; Colloid & Polymer Sci. 258, 1077–1085 (1980)

95 Vol. % $D_2O$—5 Vol. % $H_2O$
94.8 Vol. % Ethylene Glycol—5.2 Vol. % 3-Butene-2-ol
$H_2O$/Methanol—$D_2O$/Methanol (0–100%)
$H_2O$/Glycerine—$D_2O$/Glycerine (0–100%)

Examples from G. P. Langer; Colloid & Polymer Sci. 257, 522–532 (1979)

12.6 Wt. % Glycerine/$H_2O$—2.38 Wt. % Glycerine/$H_2O$

Examples from Thesis of Wulf Alex

Glycerol/$H_2O$—Glycerol/water (0.13 parts by wt. $C_3H_8O_3$/19 ml $H_2O$—0.45 parts by wt. $C_3H_8O_3$/21 ml $H_2O$.

It will be seen that the liquids used may vary widely. The principal considerations are that the liquids of the liquid pair or liquid series have different densities at ordinary temperatures and be miscible. It is also desirable that the viscosities of the respective liquid compounds used in forming the spin fluid, or the liquid mixtures used in forming the spin fluids, differ from each other by less than 1 poise at 20° C. Thus, the liquids of a liquid pair, for example, may be fully mixed solutions of the same liquid or solid solute in a solvent, but at different concentrations.

The ex situ formed spin fluid containing incompletely mixed liquids of different density and the sample fluid or mother liquid are separately and sequentially in the order named injected into the central part of the disc while spinning at the predetermined speed. A preferred manner of injecting such liquids into a disc centrifuge is clearly set forth in the book by Brian H. Kaye entitled "Direct Characterization of Fineparticles" in the Chemical Analysis Monograph, Volume 61, published by John Wiley & Sons (1981), pp. 189–226, particularly at page 204. The recommended method utilizes a hypodermic needle and syringe to inject the spin fluid and the mother liquid or sample containing the particles in suspension directly onto the back surface of the rotating centrifuge chamber. By causing the spin fluid to enter at or near the axis of the disc where the actual linear motion of the system is low, the fluid is able to flow over the back surface and up the vortex without invading the vortex of the spin fluid. The smallest hypodermic needle compatible with the particles undergoing analysis is recommended.

To test a commercial production batch of 50% solids latex, a couple of drops of the latex in a 20 to 25 ml. volume of 50:50 MeOH/water solution is conveniently used as a mother liquid. The same procedure used in developing the profiles shown in FIGS. 2, 3, 4, 5 and 6 with known particle sizes is used with unknown samples. The elapsed time to a peak is correlated thru application of Stokes' Law to determine particle size. The shape and elevation of the peak is correlated with distribution. These correlations are described in detail in the prior art mentioned above and thus are known to those skilled in the art.

What is claimed is:

1. A method for analysis of the size and/or distribution of particles emanating from a mother liquid by sedimentation in a rotating disc centrifuge which comprises the steps of forming externally of said disc a liquid spin medium containing at least two miscible liquids of different densities in substantially incompletely mixed condition whereby a density gradient is established within said spin medium, thereafter injecting said externally formed spin medium into said disc while spinning said disc at a predetermined speed, and followed by injecting a mother liquid containing particles the size and/or distribution of which are to be determined into said disc centrifuge while spinning at said predetermined speed and measuring by centrifugal sedimentation the partice size and/or distribution of the particles in said mother liquid.

2. A method as defined in claim 1 wherein the liquid of lower density is inspired through the liquid of higher density.

3. A method as defined in claim 1 wherein a plurality of externally formed spin media are formed each containing at least two miscible liquids of different densities in substantially incompletely mixed condition whereby a density gradient is established within each said spin medium, and said spin media are sequentially injected into said rotating disc in the reverse order to their respective densities.

4. A method as defined in claim 1 wherein the spinning disc centrifuge, prior to injection of the externally formed spin medium, has previously injected into the disc a layer of water circumferentially disposed therein.

5. A method as defined in claim 1 wherein the spin medium is composed of water and a $C_1$-$C_4$ alcohol.

6. A method as defined in claim 5 wherein the $C_1$-$C_4$ alcohol is methyl alcohol.

7. A method as defined in claim 5 wherein the $C_1$-$C_4$ alcohol is ethanol.

8. A method as defined in claim 1 wherein the spin medium is composed at water and a water soluble polyol.

9. A method as defined in claim 8 wherein the water soluble polyol is ethylene glycol.

10. A method as defined in claim 1 wherein the spin medium is composed of a pair of glycerol/water solutions each containing a different concentration of glycerol.

11. A method as defined in claim 1 wherein the spin medium is composed of water and an aqueous solution of a solute.

12. A method as defined in claim 11 wherein the solute is a water soluble sugar.

13. A method as defined in claim 11 wherein the solute is a mineral acid.

14. A method as defined in claim 11 wherein the solute is a ketone.

15. A method as defined in claim 11 wherein the solute is acetone.

16. A method as defined in claim 11 wherein the solute is methyl ethyl ketone.

17. A method as defined in claim 11 wherein the spin medium is formed from three liquids, at least two of which are miscible in the third, but not in each other.

18. A method as defined in claim 17 wherein the third liquid is isopropyl alcohol and the first and second are hexane and water, respectively.

* * * * *